United States Patent [19]

Rothfuss et al.

[11] 4,312,363
[45] Jan. 26, 1982

[54] SURGICAL TISSUE THICKNESS MEASURING INSTRUMENT

[75] Inventors: Robert G. Rothfuss, Bellevue, Ky.; Edwin L. Stith, Jr., Cincinnati, Ohio

[73] Assignee: Senco Products, Inc., Cincinnati, Ohio

[21] Appl. No.: 124,955

[22] Filed: Feb. 26, 1980

[51] Int. Cl.³ .............................................. A61B 5/10
[52] U.S. Cl. .................................................... 128/774
[58] Field of Search ................... 128/774, 321–325, 128/361; 33/143 C, 174 D

[56] References Cited

U.S. PATENT DOCUMENTS

| | | | |
|---|---|---|---|
| 3,008,239 | 11/1961 | Lange | 33/143 K |
| 3,740,779 | 6/1973 | Rubricuis | 33/143 C |
| 4,127,112 | 11/1978 | Sherlock et al. | 128/774 |
| 4,201,226 | 5/1980 | Phillips | 128/774 |
| 4,226,025 | 10/1980 | Wheeler | 128/774 |
| 4,233,743 | 11/1980 | Flick | 33/143 C |

FOREIGN PATENT DOCUMENTS 1330985  9/1973  United Kingdom ............. 33/143 C

OTHER PUBLICATIONS

Verel, D., et al., *The Lancet*, Oct. 29, 1960, p. 962.

*Primary Examiner*—Robert W. Michell
*Assistant Examiner*—Angela D. Sykes
*Attorney, Agent, or Firm*—Frost & Jacobs

[57] ABSTRACT

A tissue thickness measuring instrument for surgical purposes comprising a pair of opposed tissue engaging jaws. Manually graspable actuating means operatively connected to the jaws for shifting the jaws away from each other. A resilient means urges the jaws toward each other with a substantially constant predetermined force over a predetermined working range of separation distance between the jaws. At least one scale with cooperating indicator is provided in association with the jaw actuating means giving a direct reading of the thickness of the tissue being measured. The instrument may be provided with another scale by which the diameter of tubular body elements in the flaccid state can be determined.

6 Claims, 12 Drawing Figures

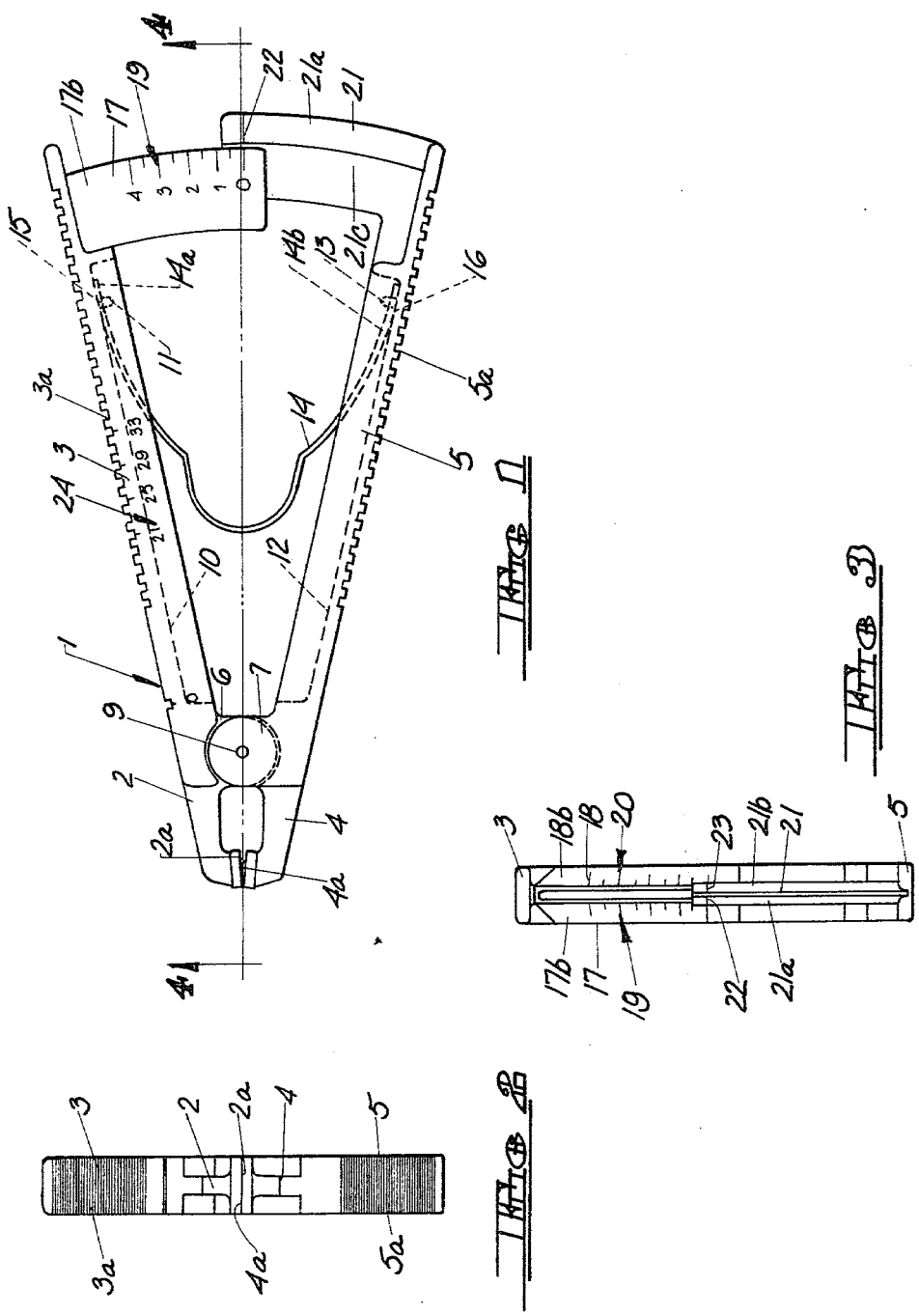

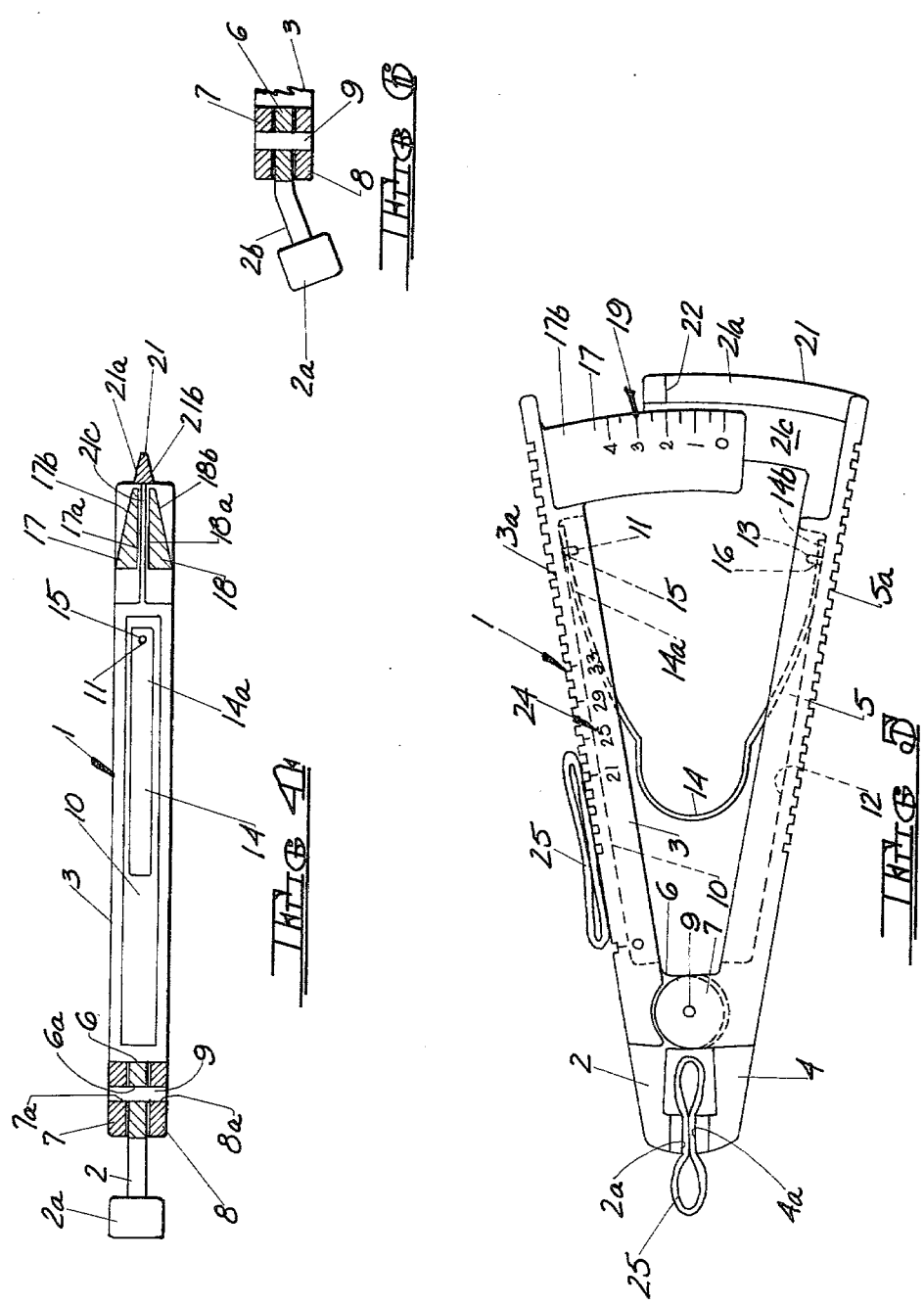

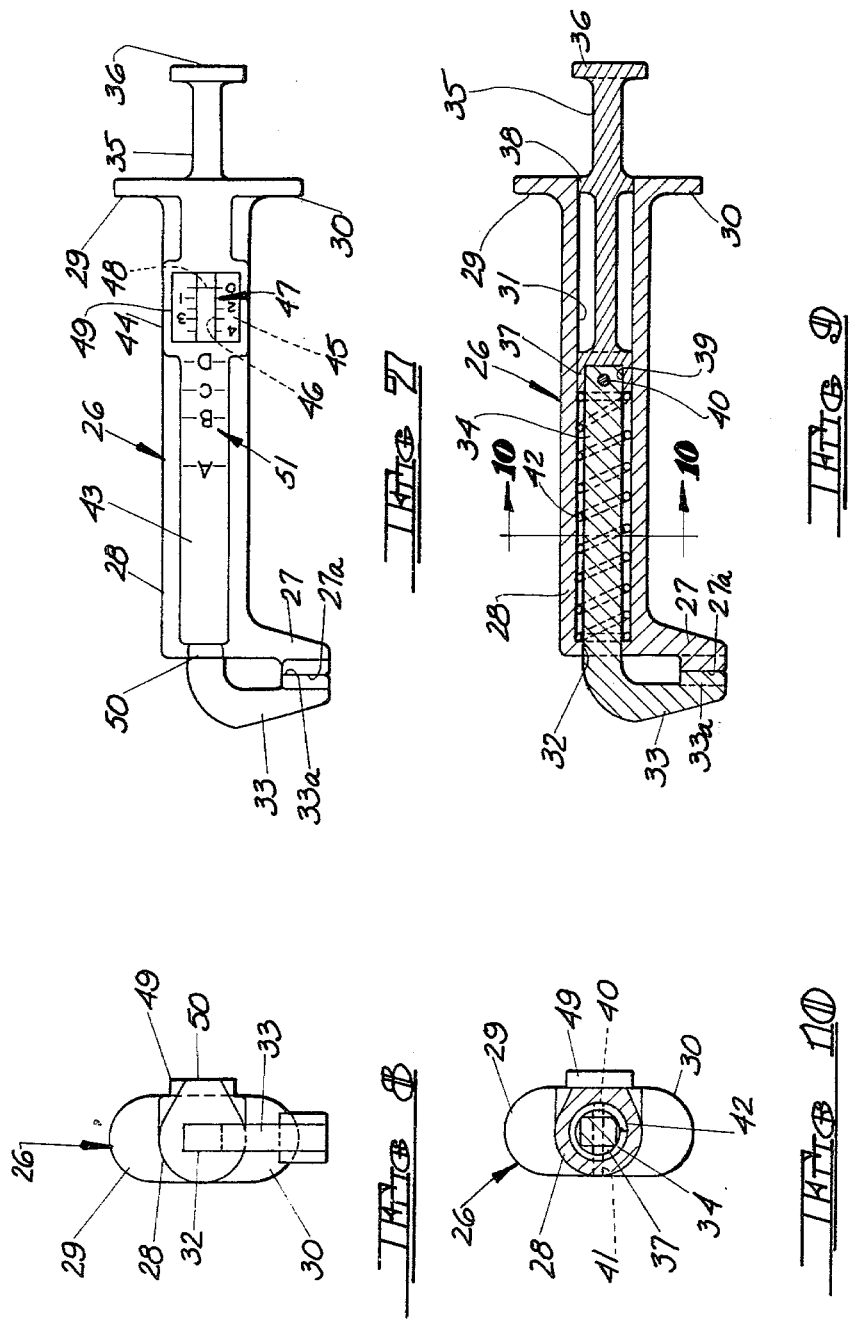

SURGICAL TISSUE THICKNESS MEASURING INSTRUMENT

TECHNICAL FIELD

The invention relates to a surgical tissue thickness measuring instrument and more particularly to such an instrument for use in conjunction with a surgical stapling instrument to determine the size of the staple to use and the proper gap to which the intrument should be set.

BACKGROUND ART

In the past decade there has been an increasing number of surgeons using staples in lieu of conventional sutures in many internal organ procedures ranging from the esophagus to the rectum. This trend is due largely to the fact that the use of stapes is much easier and a number of difficult procedures are rendered much simpler through the use of staples. Perhaps of even greater importance, however, is the fact that the use of staples is a very much faster procedure, substantially reducing the time required for suturing and, therefore, the length of time the patient must be maintained under anesthesia.

Along with the above noted advantages, surgical stapling procedures also present certain problems. For example, it is necessary to select the proper staple size for the thickness of the tissue to be joined. Furthermore, it is quite possible that even if the proper staple size is selected, the staple could be formed in the tissue either too tightly or too loosely. If the surgical staples are formed too tightly, the blood supply needed for the healing process is cut off and the tissue will become necrotic. On the other hand, if the staples are formed too loosely, then hemorrhaging and/or leakage can occur. Both too tightly and too loosely formed staples can cause serious problems and complications.

It is precisely these problems, inherent in surgical stapling, that cause the need for an instrument to measure the thickness of tissue to be joined by surgical staples. Surgical staples are available in various sizes. Many surgical stapling instruments are provided with means enabling the adjustment of the gap between the cartridge or head containing the staples and the anvil against which the staples are formed, thereby determining the amount by which the staples are clinched. If the thickness of the tissue to be joined is known, appropriately sized staples can readily be selected and the above noted gap can be properly set.

The very nature of living tissue makes it somewhat difficult to measure because of its soft, elastic and resilient properties. Studies have been conducted to determine the optimum healing pressure, for example, for intestinal tissue. The optimum healing pressure varies with various types of tissue. Lung tissue, for example, is quite different from intestinal tissue. Therefore, the tissue measuring device of the present invention would have to be designed to apply the optimum healing pressure during the tissue measuring operation for the particular type of tissue being measured. This can readily be done and the same principles and mode of operation of the tissue measuring instrument of the present invention would be involved with each type of tissue.

For purposes of an exemplary showing, the tissue measuring instrument of the present invention will be described in its application to the measurement of the thickness of intestinal tissue. Prior art workers have developed various types of intralumenal anastomosis surgical stapling instruments. Exemplary, but nonlimiting, examples of such instruments are taught in U.S. Pat. No. 3,552,626, copending application Ser. No. 890,262, filed Mar. 27, 1978 in the name of Carl T. Becht and entitled INTRALUMENAL ANASTOMOSIS SURGICAL STAPLING INSTRUMENT and copending application Ser. No. 06/124,954, filed Feb. 26, 1980 in the name of Robert G. Rothfuss and entitled INTRALUMENAL ANASTOMOSIS SURGICAL STAPLING INSTRUMENT. These instruments join the tubular body parts substantially in end-to-end relationship, engaging the tubular parts internally and removing excess portions of the tubular parts adjacent the annular set or sets of staples implanted by the instrument, through the use of a cylindrical scalpel or the like. These instruments are adapted to use cylindrical cartridges of staples of one or more sizes and are provided with means to preset the gap between the staple containing cartridge and an annular anvil member against which the staples are formed. The adjacent tubular body parts to be joined together are located within the gap. The tissue measuring instrument of the present invention is intended to be used with such exemplary surgical stapling instruments provided with gap setting means (as for example that taught in the last mentioned copending application), the calibration of which is identical to that of the tissue measuring instrument.

The tissue measuring instrument of the present invention attaches to the tissue with a clamping action, making the actual tissue thickness measurement independent of the surgeon. The instrument, during the measuring process, will clamp on the tissue to be measured with a force substantially equivalent to the above mentioned optimum healing pressure. This is true over a predetermined range of tissue thicknesses. The instrument has at least one scale and indicator means by which the tissue thickness can be readily and directly read by the surgeon. The clamping jaws of the instrument are so configured as to provide easy engagement thereby of intestinal tissue where access is limited. The instrument may be provided with a second scale from which the diameter of the intestinal lumens can be determined for selection of a cylindrical staple cartridge of the proper diameter.

DISCLOSURE OF THE INVENTION

According to the invention there is provided a tissue thickness measuring instrument for surgical uses comprising a pair of opposed tissue engaging jaws. Manually graspable actuating means are operatively connected to the jaws for shifting the jaws away from each other against the action of a resilient means which urges the jaws toward each other with a substantially constant predetermined force over a predetermined working range of separation distance between the jaws. The instrument has at least one scale with a cooperating indicator giving a direct reading of separation distance between the jaws and thus a direct reading of the thickness of the tissue being measured thereby. The instrument may be provided with another scale by which the diameter in the flaccid state of the tubular body elements to be joined can be determined.

In one embodiment of the tissue measuring instrument, the instrument is of pliers-like configuration, the jaw actuating means comprising handle elements pivotally joined together. The handle elements, at the distal end of the instrument have the cooperating scale and indicator means from which a direct reading of the tissue thickness can be observed from either side or the rear of the instrument. One of the handle elements may carry another scale from which the diameter of a tubular organ in flaccid state can be determined.

In a second embodiment of the instrument, a first jaw has a manually graspable extension of tubular form. The second jaw has an extension in the form of a plunger assembly axially shiftable within the tubular extension of the first jaw. The extension of the second jaw carries an indicator which cooperates with a scale on the extension of the first jaw for direct reading of the tissue thickness being measured. The scale may be equipped with magnifying means, as will be described hereinafter. In this embodiment of the tissue measuring instrument, the tubular jaw extension may carry another scale from which the diameter of a tubular organ in flaccid state can be determined.

BRIEF DESCRIPTION OF THE DRAWINGS

FIG. 1 is a side elevational view of one embodiment of the tissue measuring instrument of the present invention.

FIG. 2 is a front elevational view of the embodiment of FIG. 1 as seen from the left in that Figure.

FIG. 3 is a rear elevational view of the instrument of FIG. 1 as seen from the right in that Figure.

FIG. 4 is a cross sectional view taken along section line 4—4 of FIG. 1.

FIG. 5 is a side elevational view similar to FIG. 1 and illustrating the use of the instrument of FIG. 1.

FIG. 6 is a fragmentary cross sectional view similar to FIG. 4 and illustrating the provision of a laterally offset jaw.

FIG. 7 is a side elevational view of a second embodiment of the tissue measuring instrument of the present invention.

FIG. 8 is a front end elevational view of the instrument of FIG. 7 as seen from the left in that Figure.

FIG. 9 is a longitudinal cross sectional view of the instrument of FIG. 7.

FIG. 10 is a cross sectional view taken along section line 10—10 of FIG. 9.

BEST MODE OF CARRYING OUT THE INVENTION

Figure 11:
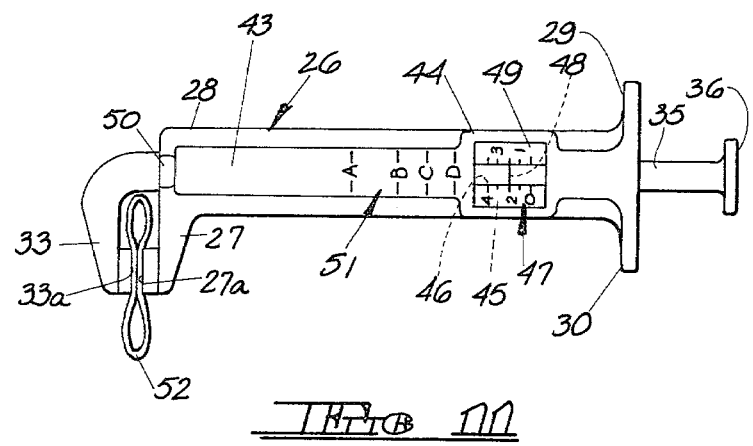
FIG. 11 is a side elevational view similar to FIG. 7 and illustrating the use of the instrument to measure tissue thickness.

A first embodiment of the tissue measuring instrument of the present invention is illustrated in FIGS. 1 through 6, wherein like parts have been given like index numerals. Reference is first made to FIGS. 1 through 4. The instrument itself is generally indicated at 1 and comprises a first jaw 2 having a rearward extension in the form of a first handle element 3 and a second jaw 4 having a rearward extension in the form of a handle element 5. At their forward ends, jaws 2 and 4 terminate in planar tissue engaging surfaces 2a and 4a, respectively.

As will be evident from FIGS. 1 and 2, the jaws 2 and 4 have a transverse thickness approximately one-third that of their respective handles 3 and 5. The first jaw 2 and handle 3 have a downwardly depending central portion 6 with a transverse perforation 6a therethrough.

The second jaw 4 and its handle 5 have a pair of upstanding members or bifurcations 7 and 8, having transverse coaxial perforations 7a and 8a, respectively. The downwardly depending element 6 of first jaw 2 and its handle 3 is adapted to be located between upstanding members 7 and 8 of second jaw 4 and its handle 5 with perforations 6a, 7a and 8a coaxial. A pivot pin 9 is located in these perforations thereby pivotally joining first jaw 2 and its handle 3 to second jaw 4 and its handle 5.

The handle 3 of first jaw 2 has an elongated groove or depression 10 formed on its inside surface. This depression 10 is shown in FIGS. 1 and 4. At the rearward end of depression 10 an upstanding stud 11 is formed. Handle 5 of second jaw 4 has a similar longitudinally extending groove or depression 12 formed on its inside surface (see FIG. 1). At the rearward end of depression 12 an upstanding stud 13 is located, the stud 13 being similar to stud 11 of handle 3. A leaf spring 14 is located between handles 3 and 5. The end 14a of spring 14 is located in the depression 10 of handle 3 and has a perforation 15 formed therein. The stud 11 extends through the perforation 15, as shown in FIGS. 1 and 4. The end 14b of spring 14 is similarly located in the groove or depression of handle 5. Spring end 14b has a perforation 16 therein through which stud 13 extends. It will be evident that spring 14 will remain in place between handles 3 and 5 by virtue of the fact that its ends 14a and 14b are located in handle grooves or depressions 10 and 12 and are engaged by studs 11 and 13, respectively. The spring 14 urges handles 3 and 5 apart, thus urging jaws 2 and 4 and their tissue engaging surfaces 2a and 4a together. FIGS. 1 through 3 illustrate the tissue measuring instrument in its normal condition when not in use.

Handle 3, at its distal end, has a pair of downwardly depending elements 17 and 18. As can most clearly be determined from FIG. 4, the elements 17 and 18 are of substantially triangular cross section. Their facing surfaces 17a and 18a are in parallel spaced relationship. Their exterior surfaces 17b and 18b slope rearwardly and toward each other. Outside surface 17b of element 17 carries indicia in the form of a scale, generally indicated at 19. Exterior surface 18b of element 18 is provided with indicia in the form of an indentical scale, generally indicated at 20.

The second handle 5 has an upstanding arcuate member 21. As can most easily be seen in FIG. 4, the member 21 has a rearward triangular edge having one surface 21a substantially coplanar with the surface 17b of element 17 and a second surface 21b substantially coplanar with surface 18b of element 18. The member 21 also has a thin web-like body portion 21c which fits just nicely between the surfaces 17a and 18a of elements 17 and 18. The surface 21a of element 21 carries an indicator line 22 cooperating with the scale 19 of element 17 (see FIGS. 1 and 3). Similarly, the surface 21b carries an indicator line 23 identical to indicator line 22 and adapted to cooperate with the scale 20 of element 18. The scales 19 and 20 are expanded at least about 3:1 for ease of reading. In the embodiment illustrated the scales 19 and 20 are expanded 4:1.

To complete the structure, the handle 3 may be serrated as at 3a so that it can be conveniently and firmly grasped in non-slip fashion by the hand of the surgeon. The handle 5 may be similarly serrated as at 5a. Optionally, the handle 3 may be provided with another scale, generally indicated at 24 in FIG. 1. The scale 24 runs longitudinally of handle 3 along its side. The other side of handle 3 may be provided with an identical scale (not shown) so that the instrument can be viewed from either side during use. The scale 24 enables the surgeon to make a quick determination of the diameter of a tubular body element to be stapled, as will be described hereinafter.

Studies have been conducted to determine the optimum healing pressure for sutured intestinal tissue. This pressure is known to be approximately 8 g/m². In the exemplary application with respect to which the tissue measuring instrument is herein being described, it has been found adequate in the measurement of intestinal tissue to design the instrument to be capable of measuring tissue thickness over a range of from 0 to 4 mm. It will be noted from FIGS. 1 and 3 that scales 19 and 20 extend over this range. The spring 14 is designed to be a constant bias spring causing jaw surfaces 2a and 4a to measure tissues located therebetween at a pressure of 8 g/mm² at ½ the working range (i.e., at 2 mm separation between the surfaces) and for all practical purposes exerting this same pressure throughout the working range of from 0 to 4 mm. The jaws 2 and 4 are so configured that their surfaces 2a and 4a will be parallel at ½ the working range (i.e., a 2 mm separation between the surfaces) to assure maximum accuracy of the tissue thickness measurement. The instrument 1 may be made of any material (including plastic, metal, combinations thereof, or the like) suitable for a surgical environment and capable of being sterilized by autoclave, ethylene oxide, irradiation or other standard methods.

FIG. 6 is a fragmentary view similar to that of FIG. 4. The embodiment shown in FIG. 6 differs from that of FIG. 4 in that the jaw (indicated at 2b in FIG. 6) is angled laterally. It will be understood that in such an embodiment the other jaw would be similarly angled. The instrument of the present invention, provided with such angled jaws, would be used in constricted areas where access is limited to insure adequate visibility.

The instrument having been described, its use may be set forth as follows. The surgeon, grasping the instrument 1 in a pliers-like fashion, squeezes handles 3 and 5, causing jaws 2 and 4 to open against the action of constant bias spring 14. For purposes of this description, the instrument will be described in its application to the tissue thickness measurement of an intestinal lumen 25 shown in FIG. 5. The jaws 2 and 4 are located about the intestinal lumen 25 as shown and, thereafter, the pressure applied to instrument handles 3 and 5 by the surgeon is released. Spring 14 will cause jaw surfaces 2a and 4a to exert a pressure on lumen 25 of about 8 g/mm². Since the surgeon is no longer applying pressure to handles 3 and 5, the direct thickness reading in millimeters on scales 19 and 20 in conjunction with indicator lines 22 and 23, respectively, is wholly independent of the surgeon. The arrangement of scales 19 and 20 is such that the direct measurement reading can be observed from either side of the instrument, or from the rear thereof.

It will be understood that in the procedure illustrated in FIG. 5 a double thickness of the intestinal lumen tissue is being measured. If two substantially identical lumens are to be joined together by the surgical stapling instrument, this reading can be used directly, being considered the sum of the tissue thickness of the two lumens to be joined. If the two lumens to be joined are of tissue of different thicknesses, each lumen can be measured in the manner shown in FIG. 5 and the resulting reading divided by 2. This will give a tissue thickness measurement for each individual lumen. The resulting thickness measurements are then added to determine the proper staple height and the proper gap to set between the instrument staple containing cartridge or head and the anvil. When necessity dictates, a single tissue thickness reading can be taken directly by inserting one of jaws 2 and 4 into the hollow interior of the lumen.

As indicated above, the instrument may be provided with the scale 24 along both sides of handle 3. It will be understood that an identical scale could be provided along both sides of handle 5, as well, as a matter of convenience. To measure the diameter of the lumen 25, the lumen, in flaccid state, is laid along the surface of handle 3 with one edge at the 0 mark of scale 24. The scale is then read at the position of the other edge of the lumen. The actual measurement in this instance is a measurement of about ½ the circumference of the lumen, which is proportional to the lumen diameter. The numbers appearing on scale 24 indicate the various circular cartridge or head diameters available for use with the intralumenal anastomosis surgical staple instrument, since the cartridge or head during the procedure is located within one of the lumens to be joined. This procedure makes the selection of proper staple cartridge or head size a simple matter, eliminating any guess work.

Reference is now made to FIGS. 7 through 12 wherein a second embodiment of the tissue measuring instrument is shown. In these Figures, like parts have been given like index numerals.

Reference is first made to FIGS. 7 through 10. The tissue thickness measuring instrument of this embodiment is generally indicated at 26. The instrument comprises a first jaw 27 having a tissue engaging surface 27a similar to the tissue engaging surface 2a of jaw 2 of FIG. 1. Jaw 27 extends laterally from the distal end of tubular body member 28. At its proximal end the tubular body member 28 has a pair of diametrically opposed, laterally extending flanges 29 and 30.

The tubular body member 28 has an axial bore 31 of uniform circular cross section throughout its length. The bore 31 extends through the proximal end of the tubular body member 28 but stops just short of the distal end thereof. The distal end of tubular body member 28 is closed and has a rectangular perforation 32 formed therein which communicates with axial bore 31.

The instrument 26 has a second jaw 33 having a tissue engaging surface 33a parallel to tissue engaging surface 27a and in abutment therewith when the instrument is not in use. The jaw 33 has an elongated shank 34 which constitutes an integral one-piece part of the jaw and which forms an angle of 90° with the jaw. As can most clearly be seen in FIG. 10, the shank 34 is of rectangular cross section. The rectangular perforation 32 in the closed end of tubular body member 28 is so sized as to just nicely receive shank 34 with a sliding fit.

The instrument 26 also has an elongated plunger, generally indicated at 25. At its proximal end, plunger 35 terminates in a head 36, engagable by the thumb of the surgeon, as will be described hereinafter. At its distal end, plunger 35 terminates in a cylindrical portion 37 having an external diameter such as to be just nicely received in bore 31 of body portion 28 with a sliding fit. The plunger 35 also has an annular flange 38. The annular flange has an outside diameter such as to be just nicely received in bore 31 with a sliding fit. It will be evident from FIG. 9 that the cylindrical end portion 37 and annular flange 38 serve to maintain plunger 35 axially aligned with respect to bore 31. Annular flange 38 is so positioned on plunger 35 that when the plunger is in its normal position as shown in FIGS. 7 and 9, the annular flange 38 will be located adjacent the proximal end of tubular body 28.

The cylincrial distal end portion 37 of plunger 35 has a recess 39 therein so sized as to accept the free end of shank 34 of jaw 33. The free end of shank 34 is attached to plunger 35 within recess 30 by a pin 40 passing through coaxial perforations in the cylindrical distal end 37 of plunger 35 and the free end of shank 34. The tubular body 28 has a perforation 41 formed therein (see FIG. 10). The perforation 41 is so located as to be coaxial with the perforations in plunger 35 and shank 34 when these elements are in their normal, unactuated conditions, as illustrated in FIGS. 7 and 9. Pin 40 is located in the coaxial perforations of plunger 35 and shank 34 via perforation 41, during assembly of the instrument.

A constant bias coil spring 42 is located within the bore 31 of tubular body 28 and surrounds shank 34 of jaw 33. One end of spring 42 abuts the end of cylindrical portion 37 of plunger 35. The other end of spring 42 abuts the closed distal end of tubular body 28. It will be evident that spring 42 serves to constantly urge shank 34 and plunger 35 to their normal positions and jaws 27 and 33 to their normal closed positions.

Reference is now made to FIGS. 7 and 10. The tubular body 28 has a flat 43 formed on one side of the instrument and extending substantially the length of the tubular body 28. The flat has an enlarged rectangular portion 44. The rectangular portion 44 of flat 43 has a centrally located, rectangular depression 45 with a longitudinally extending slot 46 bisecting the rectangular depression 45. Depression 45, to either side of slot 46, is provided with indicia in the form of a scale generally indicated at 47.

The slot 46 exposes a part of plunger 35. That part of plunger 35 which is exposed carries an indicator mark or line 48 adapted to cooperate with scale 47. Scale 47 and indicator line 48 will provide a direct reading of the distance between tissue engaging jaw surfaces 27a and 33a. To this end, it will be noted in FIG. 7, wherein the instrument is in its normal condition, that indicator line 48 is aligned with the 0 mark of the scale 47. In order to make scale 47 and indicator mark 48 more readily readable, a magnifying lens 49 is mounted in rectangular depression 45 above scale 47.

To complete the instrument, an upstanding lug 50 may be provided at the distal end of tubular body 28 adjacent the distal end of flat 43. Flat 43 may further be provided with an additional scale, generally indicated at 51. Lugs 50 and scale 51 cooperate to provide a means by which the diameter of a tubular body organ may be readily determined, as will be described hereinafter.

This second embodiment of the tissue measuring instrument having been described, its operation may be set forth as follows. Again, for purposes of an exemplary illustration, the instrument 26 will be described in its application to the measurement of intestinal lumen tissue thickness. It will be understood that the instrument can readily be designed to measure other types of tissue by selection of the proper constant bias spring 42 and provision of an appropriate scale 47. Once again, as in the instance of the embodiment of FIGS. 1 through 6, the instrument 26 is illustrated as having a working range of from 0 to 4 mm. Constant bias spring 42 is so selected and configured as to cause the jaw surfaces 27a L and 33a to apply a pressure on tissue therebetween of about 8 g/mm$^2$ over this working range. This is accomplished by utilizing a helical spring which has a very low spring rate and which is spring loaded to the proper force at a gap between jaw surfaces 27a and 33a of 2 mm. As a result, this force is for all practical purposes constant over the entire 4 mm range of the instrument.

The surgeon grasps the instrument with his thumb on plunger head 36 and his index and middle fingers gripping lateral extensions 29 and 30. By exerting a force on plunger 35, the plunger and shank 34 of jaw 33 shift axially of tubular housing 28. This separates jaws 27 and 33 against the force of constant bias spring 42. With jaws 27 and 33 open, the instrument is placed on the intestinal lumen near the selected stapling site. By removing the force on plunger 35, the instrument will grip and stay attached to the intestinal lumen. This is illustrated in FIG. 11 wherein the intestinal lumen being measured is shown at 52. Since the force on plunger 35 is released by the surgeon during the measuring operation, the measurement is independent of the surgeon. When the measurement is taken in the manner shown in FIG. 11, a double thickness of the lumen tissue is being measured. When two substantially identical lumens are to be stapled together, the reading on scale 47 can be used directly in the determination of proper staple height and surgical stapling instrument gap. When two dissimilar lumens are to be joined, each can be measured in the manner described with respect to FIG. 11 and the result for each on scale 47 is then divided by 2. This gives a tissue thickness reading for each lumen, which readings are added together to determine staple height and surgical stapling instrument gap. Once again, if necessity dictates, a direct single thickness reading may be made by inserting one of jaws 27 and 33 into the open end of the lumen being measured. For ease of reading, it is preferable that magnifying lens 49 has a magnification of at least 2×.

In the embodiment of FIGS. 7 through 10, the jaw surfaces 27 and 33 are always parallel and are capable of greater separation than surfaces 2a and 4a of jaws 2 and 4 of the embodiment of FIG. 1. Since jaws 27 and 33 are offset with respect to instrument 26, they can readily be attached to intestinal tissue in instances where access is limited.

Figure 12:
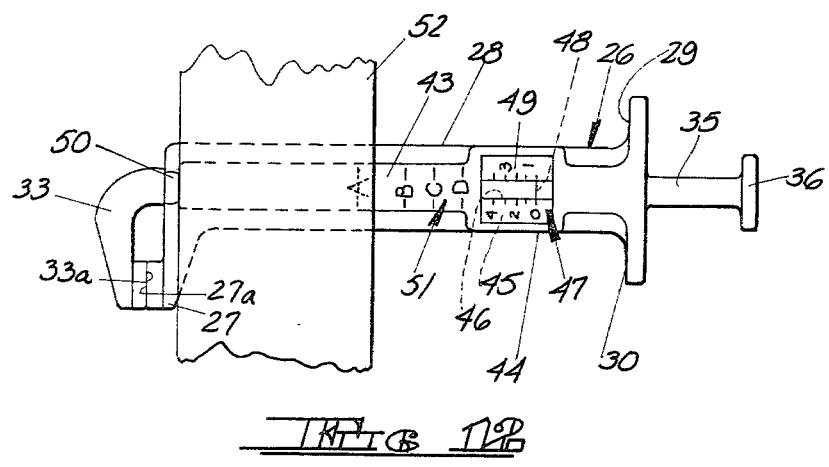
FIG. 12 is a side elevational view, similar to FIG. 11 and illustrating the use of the instrument to determine the diameter of a tubular organ.

The scale 51, as indicated above, is intended for use in the measurement of the diameter of an intestinal lumen or other tubular body organ. The use of scale 51 is illustrated in FIG. 12. The lumen, again indicated at 52, is laid along the flat 43 in flaccid state, with one of its edges against upstanding lug 50. The position of the other edge of the lumen along scale 51 can then be used to give a direct reading along the scale. As in the instance of the embodiment of FIG. 1, this reading is actually a reading of approximately ½ the circumference of the lumen 52. However, since the circumference bears a direct and well known relationship to the diameter, the scale 51 can be appropriately marked. The scale 51 could be marked in numerals indicating millimeters, as in the case of the embodiment of FIG. 1. The scale may also be marked with other indicia. In the embodiment shown in FIG. 12, the scale is shown in alphabet letters, each relating to an available cylindrical surgical staple cartridge or head of a particular diameter.

It would be within the scope of the present invention to provide the tissue measuring instrument of FIGS. 7 through 12 with more than one scale 47 and more than one scale 51, located appropriately about the periphery of tubular body 28. This would allow direct reading of tissue thickness and tubular body organ diameter at more than one position of the instrument 26.

Modification may be made in the invention without departing from the spirit of it.

What is claimed is:

1. A pliers-like tissue thickness measuring instrument for surgical purpose comprising a pair of first and second opposed tissue engaging jaws, first and second elongated handles pivotally joined together, said first handle terminating in said first jaw and said second handle terminating in said second jaw, said handles being so configured as to shift said first and second jaws away from each other over a predetermined working range of separation distance between said first and second jaws when said handles are pivoted toward each other, resilient means to urge said first and second jaws toward each other with a substantially constant predetermined force throughout said working range, a pair of arcuate members extending from the free end of said first handle in side-by-side parallel spaced relationship toward the free end of said second handle, a single arcuate member extending from said free end of said second handle toward said free end of said first handle, said single arcuate member having a first portion slidable between said pair of arcuate members of said first handle and a second portion slidable along those edges of said pair of members furthest from said jaws when said handles are shifted toward and away from each other to shift said jaws away from and toward each other, each of said pair of members bearing a scale representing said working range, said second portion of said single member having a pair of indicators each cooperating with one of said scales to give a direct reading of distance between said first and second jaws.

2. The structure claimed in claim 1 wherein said working range is from 0 to 4 mm and said resilient means is such as to cause said first and second jaws to exert a substantially constant pressure of tissue therebetween of 8 g/mm$^2$ throughout said working range whereby said instrument can be used to measure the thickness of intestinal tissue.

3. The structure claimed in claim 1 wherein at least one of said handles has a scale marked on at least one side thereof, said scale being so devised as to give a diameter reading of a tubular body organ laid therealong in flaccid state.

4. A pliers-like tissue thickness measuring instrument for surgical purposes comprising a pair of first and second opposed tissue engaging jaws, first and second elongated handles pivotally joined together, and first handle terminating in said first jaw and said second handle terminating in said second jaw, said handles being so configured as to shift said first and second jaws away from each other over a predetermined working range of separation distance between said first and second jaws when said handles are pivoted toward each other, a constant bias leaf spring located between said first and second handles with its ends affixed to said first and second handles to urge said first and second jaws toward each other with a substantially constant predetermined force throughout said working range, a pair of arcuate members extending from the free end of said first handle in side-by-side parallel spaced relationship toward the free end of said second handle, a single arcuate member extending from said free end of said second handle toward said free end of said first handle, said single arcuate member having a first portion slidable between said pair of arcuate members of said first handle and a second portion slidable along those edges of said pair of members furthest from said jaws when said handles are shifted toward and away from each other to shift said jaws away from and toward each other, each of said pair of members bearing a scale representing said working range, said second portion of said single member having a pair of indicators each cooperating with one of said scales to give a direct reading of the distance between said first and second jaws.

5. The structure claimed in claim 4 wherein at least one of said handles has a scale marked on at least one side thereof, said scale being so devised as to give a diameter reading of a tubular body organ laid therealong in flaccid state.

6. The structure claimed in claim 4 wherein said working range is from 0 to 4 mm and said resilient means is such as to cause said first and second jaws to exert a substantially constant pressure on tissue therebetween of 8 g/mm$^2$ throughout said working range whereby said instrument can be used to measure the thickness of intestinal tissue.

* * * * *